United States Patent [19]

Draenert

[11] Patent Number: 4,838,795

[45] Date of Patent: Jun. 13, 1989

[54] ARTIFICIAL JOINT COMPONENTS FOR TEACHING, RESEARCH AND VISUAL AIDS

[76] Inventor: Klaus Draenert, Gabriel-Max-Strasse 3, D-8000 Munich 90, Fed. Rep. of Germany

[21] Appl. No.: 106,139

[22] Filed: Oct. 8, 1987

Related U.S. Application Data

[63] Continuation of Ser. No. 799,392, Nov. 19, 1985, abandoned.

[30] Foreign Application Priority Data

Nov. 19, 1984 [DE] Fed. Rep. of Germany ....... 8433918

[51] Int. Cl.$^4$ .......................... G09B 23/28; A61F 2/32
[52] U.S. Cl. ........................................ 434/274; 623/23
[58] Field of Search ...................... 623/22, 23; 434/274

[56] References Cited

U.S. PATENT DOCUMENTS

| | | | |
|---|---|---|---|
| 3,658,056 | 4/1972 | Huggler et al. | 623/22 X |
| 3,893,196 | 7/1975 | Hochman | 623/23 X |
| 4,200,995 | 5/1980 | Trella | 434/274 |
| 4,221,623 | 9/1980 | Heissler et al. | 623/23 X |
| 4,520,511 | 6/1985 | Gianezio et al. | 623/23 |
| 4,535,487 | 8/1985 | Esper et al. | 623/22 |

OTHER PUBLICATIONS

"Authentic Anatomical Reproductions and Patient Simulators", Medical Plastics Laboratory Inc. 1978; p. 13.

Primary Examiner—Richard J. Apley
Assistant Examiner—Alan W. Cannon
Attorney, Agent, or Firm—Kinney & Lange

[57] ABSTRACT

The invention relates to artifical joint components in total prostheses for teaching, research and as visual aids. The outer form and structure of the joint components is the equivalent of conventional joint components; they consist of easily separable material, such as injection moulded plastic or casting resin. These joint components can be used in basic research and in surgery courses to teach and further develop new operation techniques and to evaluate results of surgery simply and with certainty, since the bone is opened up together with the implant using a simple belt saw. Immediately thereafter, the results of the operation can be evaluated.

6 Claims, 2 Drawing Sheets

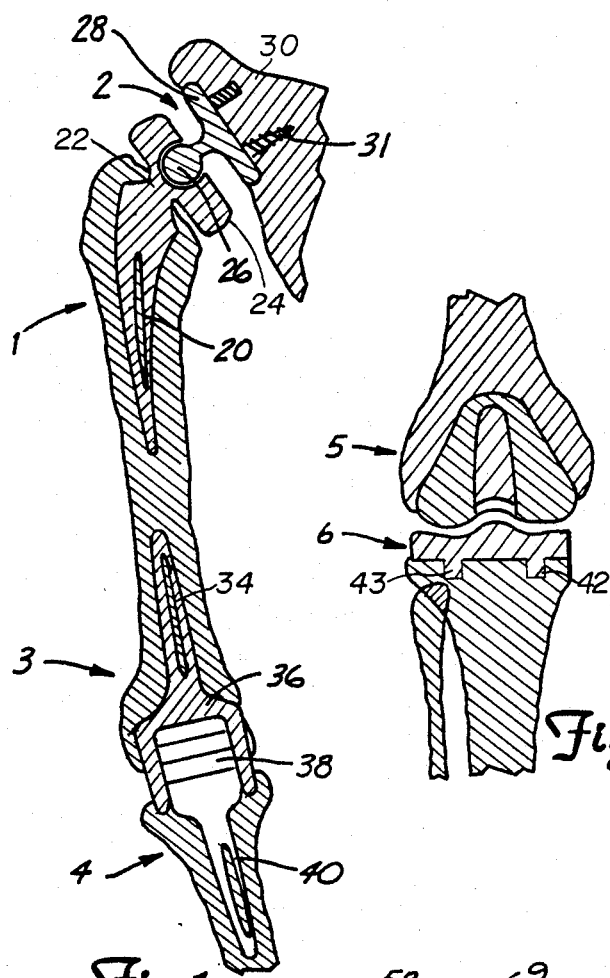
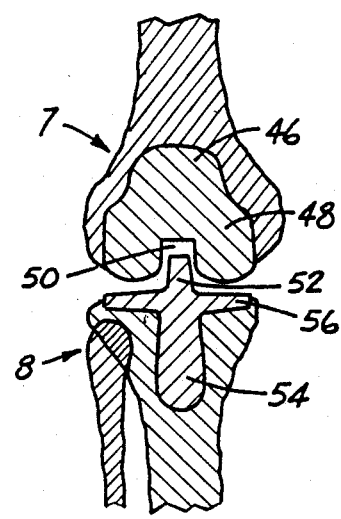
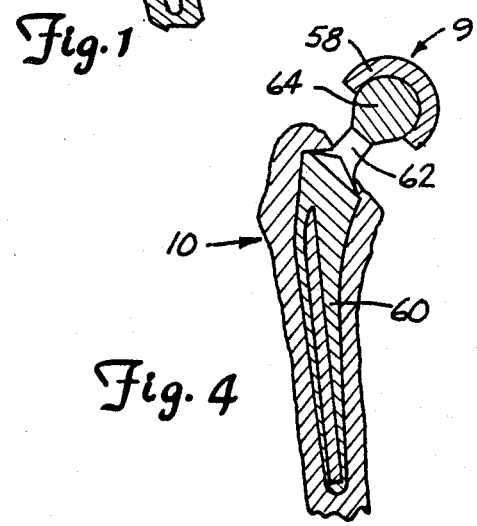
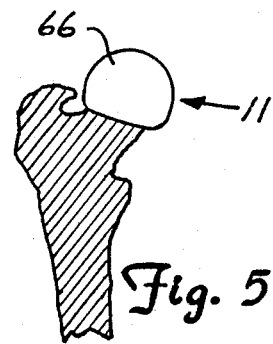

ARTIFICIAL JOINT COMPONENTS FOR TEACHING, RESEARCH AND VISUAL AIDS

This is a continuation of Ser. No. 06/799,392 filed 11/19/85, now abandoned.

TECHNICAL FIELD OF THE INVENTION

The invention relates to artificial joint components for teaching, research and visual aids.

BACKGROUND OF THE INVENTION

When joint replacements were introduced in the orthopeadic treatment and surgery of the locomotor system, physicians were confronted with technical and surgical problems which they had not been prepared for at medical school.

Surgical processes forming the basis of such new technologies in medicine can only be practiced successfully if the risks, incorrect planning and errors during surgery and in pre-operative and follow-up treatment are taught, presented and substantiated.

Histological material was obtained during operations to replace prostheses. A critical evaluation of artificial hip joint implants with poor results showed that the main reason for prosthesis loosening was the incorrect implantation of the prosthesis' components.

Moreover, macroscopic and microscopic, histological findings in joint implants—some of which had been in place for over 20 years and had been taken from deceased patients—showed that the cementing techniques and their results often differed greatly and were often the major reason for poor results.

Errors made when inserting a prosthesis can be due, for example, to the poor or incorrect preparation of the prosthesis' bone bed. The goal of improved implantation techniques is very similar to that of dental implants: to provide an implant bed which is as clean and dry as possible.

Examining the end of the medullary canal, bone cement penetration, anchoring in the proximal femur, the position of the prosthetic components, avoiding the creation of gaps while the bone cements are hardening and removing excess cement while and after the cement components harden are only a few of the criteria the surgeon must master and be able to evaluate.

Evaluating and making use of the pressure build-up in the cement applicator during the application and hardening of the bone cements are of utmost importance in improving cementing techniques.

The modern methods used in the treatment of fractures and in joint replacement are taught in courses in surgery. It is primarily practicing surgeons in orthopeadics and traumatology who are invited to these courses. These courses teach, above all, preparing the bony support, anchoring techniques for the prosthetic components and the position of the prosthetic components in the bone; they also deal with potential errors made in these procedures.

Evaluating the results of surgery in such courses encounters a particular obstacle, however: Implants inserted in bone can only be judged with precision if the bone and the implant are both cut open together. Most prosthetic components are made of a highly resistant material such as metal, ceramic or high-strength plastic. As a result, this is impossible due to the highly complicated separation process.

In research and in the laboratory, it is not possible, for economic and procedural reasons, to perform relatively large series of implantations with known prostheses in order to perform systematic research on the surgical techniques and potential errors.

SUMMARY OF THE INVENTION

It is an object of the invention to provide artificial joint components with which the above-mentioned disadvantages can be eliminated. It is another object of the invention to provide artificial joint components with which new operational techniques can be taught and further developed in relatively large series in basic research and in courses in surgery, and the results of surgery can also be judged easily and with certainty.

The invention thus relates to joint components in total prostheses for teaching, research and as visual aids, the external shape and structure of which is the equivalent of common joint components wherein the joint components consists of an easily separable material.

DESCRIPTION OF THE PREFERRED EMBODIMENTS

The invention starts with the basic idea of developing joint components made of a material which can be easily cut or sawed. They can be produced, in particular, as exact casts or negative models from common joint components. If such joint components are implanted in surgery courses, the bone together with the implant can be cut open during the course with a simple belt saw. The results of surgery can then be judged. This is of great didactic value. Materials especially suited for this purpose include plastics such as injection moulded plastics and casting resins. "Common artificial joint components" does not only mean joint components which are common today. This also refers to joint components or prostheses to be developed in the future and which can be used in surgery as joint replacement.

The stability of the prosthetic components' material only plays a subordinate role, since it is the prostheses' volume effect which is of almost exclusive importance——and not its mechanical resistance—for the application and anchoring technique used in prosthetic components. Plastic prostheses are much better suited for courses than metal prostheses, since the prostheses implanted in the bone can be sawed in half very quickly along their medial seam with a simple belt saw. In this way, the results of the operation, i.e. in particular the cement coat formation, the cement penetration, the sinking of the cement into the medullary cavity, the application of the plug closing the medullary cavity, the anchoring in the proximal femur for instance, the position of the prosthesis, the cement coat surrounding the prosthetic components, etc. can be judged with precision and evaluated critically.

The plastic prostheses for training have an additional advantage: They can be produced in all colors which increases the visual impression and thus makes them easier to remember. The results of the operation can be presented especially impressively if both the plastic used for the implant and the cement are colored, thus making it possible to observe the cement layers and the dynamic flow behavior. If the implant and the cement can be separated easily, the results of the operation can be documented simply and quickly for all participants in the course.

Priority is given to the application or admixture of colors which do not splinter off when sawed and which prevent the plastics from cracking.

The use in courses of the joint components in accordance with the invention has an additional advantage: Due to their economy, every participant can perform a series of operations and can take the results of the operations home as a finished visual aid. In this way, the participants can in turn pass on the results of the operations in larger or smaller further training groups. This is what makes it possible to achieve the goal set: to improve the clinical short-term, and in particular, the long-term results of joint replacement surgery.

Moreover, due to their reasonable price, the joint components in accordance with the invention can also be used in research. It is possible to perform relatively large series of implantations to systematically research operation techniques and potential errors which can be made when implanting joint components. Such series implantations have not been possible, or have only been possible to a limited extent, to date due to the expensive material involved and the time-consuming preparation and separation techniques required.

All of the conventional and common joint components, e.g. cups and stem prostheses, have been copied for the joint components in accordance with the invention. The material used for the joint components in accordance with the invention must be of sufficient mechanical strength and resistance and capable of being shaped precisely in order to simulate the results of surgery with prostheses actually used in surgery; it must also be possible to separate the material with conventional saws.

The cup prostheses are best produced in casts. Commercial casting resins ensure that these cast models exhibit high precision. Moreover, these prosthetic components can easily be produced in various colors. The following casting resins are preferred: epoxy casting resins, polyester resins, acrylic resins and phenolic resins.

Stem prostheses are best produced using the somewhat more expensive injection moulding process. An injection mould is made and the injection moulding machine is used for series production. This makes it possible to produce mechanically resistant prostheses in all colors for training purposes. The following plastics are preferred for injection moulding: styrene butadiene, styrene acrylic nitrile, polyvinylidene fluoride, polyurethane, polystyrene, polyphenylene sulphide, polypropylene, polyoxy methylene, polymethyl methacrylate, polyethylene, polycarbonate, polybutene terephthalate, polyamide and acrylic nitrile butadiene styrene.

The plastic joint component, in accordance with the invention, for total prostheses to be used for teaching, research and as visual aids can copy all common and conventional prosthetic components; they present the same outer form and structure. A number of conventional prosthetic components will be described in more detail below on the basis of the figures. The joint components in accordance with the invention made of injection moulded plastics or casting resins present the same outer structure as the conventional prosthetic components.

BRIEF DESCRIPTION OF THE DRAWINGS

FIG. 1 shows conventional shoulder joint and elbow joint components,

FIG. 2 shows conventional knee joint components with a "sliding prosthesis",

FIG. 3 shows conventional knee joint components with a hinged joint,

FIG. 4 shows a conventional total prosthesis of the hip joint,

FIG. 5 shows a total prosthesis of the hip joint formed by two cups,

FIG. 1 presents a conventional shoulder joint component 1 with a tapered stem 20 inserted in the shaft of the humerus, an adjacent tapering 22 with a plate or disc 24 fitted onto it. Said plate or disc presents a nearly spherical recess near its center. Component 1 inserted in the shaft of the humerus cooperates with the shoulder joint component 2. Sphere 26 engaged in the recess in plate 24 has a tapered central section and a plate 28. Said plate 28 is preferably anchored into the shoulder with two pegs 30, 31. In accordance with the invention, components 1 and 2 are made of injection moulded plastic or casting resin.

Figure 6:
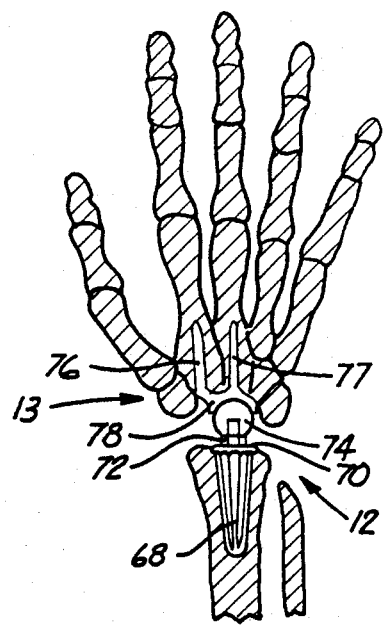
FIG. 6 shows conventional hand joint components.

There are other common shoulder joint components in addition to those presented in FIG. 1. The component inserted in the shaft of the humerus in this shoulder joint prosthesis presents a tapered stem with a nearly semi-spherical head placed on it. The head is generally somewhat broader than the stem and thus a collar is formed at the transition between the head and the stem. Said collar rests on the humerus. The first component inserted in the shaft of the humerus cooperates with the second shoulder joint component which takes the shape of a narrow socket or cup. The inside of the socket is shaped like part of a spherical surface. It takes up the spherical circumference of the first component's head. The second component's socket is generally made of metal or a very resistant plastic and is screwed into the bone. In accordance with the invention, the first and second components consist of injection moulded plastic or casting resin.

Hinged joints are generally used on the elbow. The stem or tang of the elbow joint component 3 has been inserted in a recess formed by the bone marrow space of the humerus; that of component 4 in the bone marrow space of the ulna. The radius with its epiphysis is generally removed. There is a broadening 36 at the end of the stem or tang 34 in component 3 inserted in the humerus. Said broadening presents a central, nearly rectangular recess which takes up the head 38 formed in component 4 inserted in the ulna. Component 4 may present an enveloping collar or a lock between its stem 40 and its head 38. Said collar or lock rests on the ulna.

FIG. 2 presents a type I sliding knee joint prosthesis. The knee joint component 5 is anchored in the distal femur. The cartilaginous joint surface is replaced to a greater or lesser extent. The component may be screwed in place, but generally it is anchored by means of two or more short pins that fit into recesses in the bone. Its form is an imitation of the form taken to the bone with the distal femur. The knee joint component 6 opposite component 5 takes the shape of the tibial plateau; it is generally made of plastic and is passively joined by two or more pins, such as pins 42 and 43, that fit into recesses in the bone.

FIG. 3 presents a type II conventional knee joint replacement. Like the elbow joint, it takes the shape of a hinged joint. It is anchored in a recess in the bone, preferably with bone cement, with two stems, both above and below. Shaft 46 of component 7, which is anchored in the femur, presents a head 48 at its distal end. The head 48 has a central, nearly rectangular recess 50 which takes up a similarly shaped projection or lug 52 on a component 8 which is anchored in the tibia with a stem or tang 54 that fits into a recess in the bone. Component 8 presents a plate-shaped broadening 56 between stem 54 and lug 52 at the tibial plateau.

The conventional total hip prosthesis in accordance with FIG. 4 includes component 9 which is a plastic socket 58 anchored in the hip bone by means of bone cement or one, two or more pins. Joint component 10 in the shaft of the femur is a stem prosthesis, with an articular head, inserted in the bone. Stem 60 in component 10 can be straight or arched. An encircling edge or collar resting on the femur may be formed between the stem and the nearly spherical articular head resting on a cylindrical continuation 62 of the stem. Component 10 is fixed in the femur either with bone cement or a self-locking mechanism. In the latter case, no encircling edge or collar is formed.

FIG. 5 presents another type of total hip joint replacement (double cup). In this case, only the cartilaginous articular surface is replaced. In joint component 11, a metal or ceramic cup 66 is cemented or screwed onto the head of the femur. A second plastic cup is cemented or screwed in the region of the acetabulum. Said cup takes up component 11. It is not shown in FIG. 5.

The type of joints known from the elbow are also used in the hand joint. A sphere is generally inserted between the two joint components. In accordance with FIG. 6, hand joint component 12 presents a stem 68 anchored in the radius, preferably with a small collar 70 at the distal end of the ulna, a short, preferably cylindrical center part 72 and a head 74. The head 74 is nearly spherical and rests directly on the center part 72 with its flatter end. The hand joint component 13 is anchored like a shaft with two or more pins 76, 77 in the wrist and metacarpus. The two pins 76, 77 are fork-shaped and are connected with one another by the base 78 in hand joint component 13. The base 78 presents a nearly central recess shaped like a spherical section. It takes up part of the spherical head 74 in hand joint component 12. The height of said spherical section is approximately one-half to two-thirds of the radius of head 74. The recess is formed on the base 78 approximately as an extension of one of the two pins 77.

In addition to the joint components presented in FIGS. 1-6, joint replacement at the finger joints and the ankle is also known.

The finger joints are generally hinged joints with the prosthetic components anchored on both sides in the diaphysis.

The conventional ankle joint replacement takes on the same form as the type I sliding knee joint prosthesis shown in FIG. 2.

All of the artificial joint components mentioned above, as well as all other known joint components, are made of easily separable material such as injection moulded plastic or casting resins in accordance with the invention. The material can be easily cut or sawed to form cross-sections of the bone and joint component. They are used for teaching and research. The advantages mentioned above, in comparison with conventional joint components made in particular of metal, are achieved.

Figure 7:
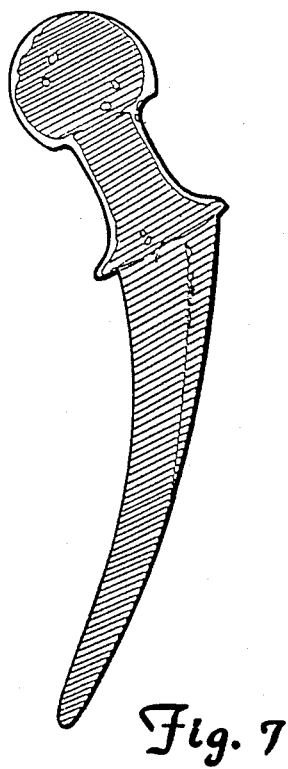
FIG. 7 shows a standard Müller prosthesis produced by injection moulding in accordance with the invention.

The Standard Müller prosthesis, produced by injection moulding, shown in FIG. 7 is the equivalent of joint component 10 in FIG. 4. It has an arched, outwardly tapering stem, a collar resting on the femur during implantation, a nearly cylindrical central part and a nearly spherical head. The head flattens towards the central part.

Figure 8:
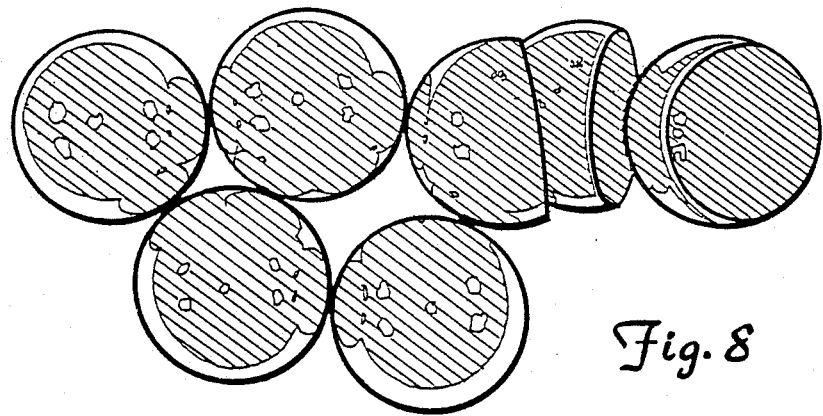
FIG. 8 shows a Wagner cup produced by the casting process in accordance with the invention.

FIG. 8 presents Wagner cups produced by the casting process in accordance with the invention.

The prostheses, for training purposes, in accordance with the invention shown in FIGS. 7 and 8 are copies of the prostheses in FIGS. 1-6. They can be used in the following areas:

educational courses for practicing orthopaedic surgeons and surgeons courses at medical schools manufacturers' development laboratories basic research institutes at universities and development institutes visual aids for students' and nurses' further training phantom models for pre-operative plans phantom models for marketing and advertising departments' macroscopic and microscopic documentation advertising gift from manufacturers of prostheses and biomaterials such as bone cement.

The cast and moulded plastic prostheses in accordance with the invention exhibit decisive advantages, compared with normal implants, for training and research purposes, in particular in surgery courses on joint replacement surgery.

The prostheses in accordance with the invention can be produced at a reasonable cost and can be used everywhere in course programs, as visual aids and in modelling engineering. Moreover, they can be processed with all common separation techniques and can be sawed open to evaluate the results of surgery.

Cementing courses with an evaluation of the results were virtually impossible prior to the plastic joint components in accordance with the invention. They open up new routes for documentation in marketing and advertising departments, for instruction to users and for teaching and further education.

The plastic prostheses in accordance with the invention can preferably be used in systematic basic research as well. They permit rapid and reasonably priced use of the material. Systematic comparative studies can be performed to present anchoring of various types of prostheses. In this way, the possibilities and weakness of the cementing results for each type of prosthesis can be established.

I claim:

1. An individualized simulated joint prosthetic device for teaching, research and visual aids comprising:

a bone portion separate from a body having a central cavity in at least an end portion where a simulated artificial joint component is to be positioned and cemented in place;

a simulated artificial joint component initially separated from the bone portion and made of easily sawable material selected from a group consisting of injection moldable plastic and casting resin mounted on said bone portion at the end portion thereof at a position where an actual artificial joint component would be positioned on a similar bone portion in a body; and cement means for holding the simulated artificial joint component in position on the bone end portion in the cavity in the bone used for such simulated artificial joint component to form the simulated prosthetic device, said prosthetic device being sectioned to form an exposed planar surface which passes through the bone portion, and the simulated artificial joint component and the cement means to permit visual inspection of the relative positioning of such simulated artificial joint component and cement means in the cavity of the bone portion.

2. A prosthetic device made in accordance with claim 1 characterized in that the synthetic material is a plastic selected from the group consisting of styrene butadiene, styrene acrylic nitrile, polyvinylidene flouride, polyurethane, polystyrene, polyphenylene sulphide, polypropylene, polyoxy methylene, polymethylmethacrylate, polyethylene, polycarbonate, polybutene terephthalate, polyamide and acrylic nitrile butadiene styrene.

3. A prosthetic device made in accordance with claim 1 characterized in that the simulated artificial joint component is colored distinctively with respect to the bone portion.

4. The prosthetic device of claim 1 wherein the simulated artificial joint component has a longitudinally extending tang which fits into a recess in the bone.

5. The device of claim 1 wherein said planar surface is formed by sawing through a bone portion enclosing the cement means and portions of the simulated artificial joint component.

6. A prosthetic device in accordance with claim 5 characterized in that the simulated artificial joint component comprises a member to be anchored in a femur, which presents an arched, tapered stem, a substantially cylindrical center portion, and a head forming a substantial portion of a sphere, and a disc-like collar between the stem and the center portion that is of larger diameter than the stem and the center portion at the junction thereof.

* * * * *